United States Patent
Theoharides (10) Patent No.: US 7,923,043 B2
(45) Date of Patent: *Apr. 12, 2011

(54) METHOD FOR PROTECTING HUMANS AGAINST SUPERFICIAL VASODILATOR FLUSH SYNDROME

(75) Inventor: Theoharis C. Theoharides, Brookline, MA (US)

(73) Assignee: Theta Biomedical Consulting & Development Co., Inc., Brookline, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/151,268

(22) Filed: May 6, 2008

(65) Prior Publication Data
US 2009/0148543 A1  Jun. 11, 2009

Related U.S. Application Data

(63) Continuation-in-part of application No. 11/999,991, filed on Dec. 10, 2007, which is a continuation-in-part of application No. 11/651,161, filed on Jan. 10, 2007, now Pat. No. 7,759,307, which is a continuation-in-part of application No. 10/811,828, filed on Mar. 30, 2004, now abandoned.

(51) Int. Cl.
*A61K 36/00* (2006.01)
*A61K 36/63* (2006.01)
(52) U.S. Cl. .......................... 424/725; 514/8
(58) Field of Classification Search .......... None
See application file for complete search history.

(56) References Cited

U.S. PATENT DOCUMENTS

| | | | |
|---|---|---|---|
| 5,223,257 A | 6/1993 | Arora |
| 5,250,529 A | 10/1993 | Theoharides |
| 5,260,335 A | 11/1993 | Wagner et al. |
| 5,648,355 A | 7/1997 | Theoharides |
| 5,795,905 A | 8/1998 | McCarthy et al. |
| 5,804,594 A | 9/1998 | Murad |
| 5,855,884 A | 1/1999 | Theoharides |
| 5,876,744 A | 3/1999 | Della Valle et al. |
| 5,972,999 A | 10/1999 | Murad |
| 5,980,865 A | 11/1999 | Ahmed |

(Continued)

FOREIGN PATENT DOCUMENTS

EP    0426479    5/1991

(Continued)

OTHER PUBLICATIONS

Papaloidis et al. The Flavonoid Luteolin Inhibits Niacin-Induced Flush; British Journal of Pharmacology (2008) 153, pp. 1382-1387.*

(Continued)

*Primary Examiner* — Patricia Leith
(74) *Attorney, Agent, or Firm* — Wilmer Cutler Pickering Hale & Dorr LLP.

(57) ABSTRACT

Methods for protection of a human from SVFS comprise the administration of a flavonoid compound of the basic structures 2-phenyl-4H-1-benzopyran or 2-phenyl-4-keto-1-benzopyran or glycosides thereof, alone or, optionally, together with one or more of an olive kernel extract, a non-bovine sulfated proteoglycan, bitter willow extract, a D-hexosamine sulfate, S-adenosylmethionine, folic acid, vitamin B12 and a serotonin inhibitor. Such treatment prevents, reduces or eliminates SVFS in patients receiving as much as 300-3000 mg/day of niacin therapeutically, whether administered prior to, or along with, an anti-SVFS composition.

10 Claims, 6 Drawing Sheets

Time course of the inhibitory effect of pretreatment with luteolin (4.3 mg per rat). Luteolin was given at the time points shown before, or at the same time as (shown as 0 h), the single i.p. niacin injection (7.5 mg per rat). Increases in ear temperature (n=3) were measured 45 min after niacin treatment. All pretreatments produced statistically significant inhibition, compared to a control rat injected with 0.5 ml olive oil and 7.5 mg niacin (* $P<0.001$).

U.S. PATENT DOCUMENTS

| | | | |
|---|---|---|---|
| 5,994,357 A | 11/1999 | Theoharides | |
| 6,020,305 A | 2/2000 | Theoharides | |
| 6,132,724 A * | 10/2000 | Blum | 424/725 |
| 6,136,795 A | 10/2000 | Florio | |
| 6,162,787 A | 12/2000 | Sorgente et al. | |
| 6,211,195 B1 | 4/2001 | Webb et al. | |
| 6,586,448 B1 | 7/2003 | DeNinno et al. | |
| 6,689,748 B1 | 2/2004 | Theoharides | |
| 6,765,008 B1 | 7/2004 | Chen | |
| 7,482,029 B2 * | 1/2009 | Cohen | 424/725 |
| 2001/0000340 A1 | 4/2001 | Chen et al. | |
| 2002/0146393 A1 | 10/2002 | Bell et al. | |
| 2005/0220909 A1 | 10/2005 | Theoharides | |
| 2006/0210551 A1 | 9/2006 | Lindsberg et al. | |
| 2007/0141187 A1 | 6/2007 | Theoharides | |

FOREIGN PATENT DOCUMENTS

| | | |
|---|---|---|
| GB | 2105193 | 9/1984 |
| WO | WO-9833494 | 8/1998 |
| WO | WO-0078320 | 12/2000 |

OTHER PUBLICATIONS

Phillipson, J. New Drugs From Nature—It Could Be Yew; Phytotherapy Research 13 (1999) pp. 2-8.*
Revilla et al. Comparison of Several Procedures Used for the Extraction of Anthocynains From Red Grapes; J. Agric. Food Chem. 1998, 46, pp. 4592-4597.*
International Search Report and Written Opinion, International Patent Application No. PCT/US08/86059, mailed Jan. 26, 2009 (2 pages).
Russell, A.L. and McCarty, M.F. "Glucosamine for migraine prophylaxis?" Medical Hypotheses, 55(3): 195-198 (2000).
Matsuda, K. et al., "Inhibitory Effects of Sialic-Acid- or N-Acetylglucosamine-Specific Lectins on Histamine Release Induced by Compound 48/80, Bradykinin and a Polyethylenimine in Rat Peritoneal Mast Cells," Jpn. J. Pharmacol., 64: 1-8 (1994).
Trichopoulou, A. et al., "Cancer and Meditarranean Dietary Traditions," Cancer Epidemiology, Biomarkers, & Prevention, vol. 9: 869-873 (Sep. 2000).
Theoharides, T.C., "The Mast Cell: A Neuroimmunoendocrine Master Player," Int. J. Tiss. Reac. XVIII(1), 1-21 (1996).
Theoharides, T.C., "Histamine2 (H2)-Receptor Antagonists in the Treatment of Urticaria," Drugs 37: 345-355 (1989).
Theoharides, T. "Mast Cells and Migraines," Brief Proposal, (1983).
Morrow, J. et al., "Indentification of Skin as a Major Site of Prostaglandin D2 Release Following Oral Administration of Niacin in Human," J. Invest. Derm., vol. 98(5): 812-815 (1992).
Weston, A. et al., "Terminal Ileal Mucosal Mast Cells in Irritable Bowel Syndrome," Dig. Diseases and Sci., vol. 38(9): 1590-1595 (Sep. 1993).
Shapiro, G. et al., "Cromolyn Sodium: A Review," Pharmacotherapy, vol. 5(3): 156-170 (May/Jun. 1985).
Database WPI: 2001-358435—XP002221703, "Compositions comprising hyaluronic acid and flavonoids," (2 pages).
International Search Report issued for PCT/US02/00476, dated Dec. 16, 2002 (6 pages).
Parodi et al., Arch. Psicol. Neurol. Psichiatr. vol. 49(3): 299-303 (1988).
Split et al., "Ketotifen in the Treatment of Chronic Cluster Headache," Headache, vol. 24(30: 147-148: 1984).
Unlisted Drugs, vol. 20(11): 167 (Nov. 1968).
Debeuckelaere, et al., "Systemic Mast Cell Disease: A review of the literature with special focus on the gastrointestinal manifestations", Acta clinica Belgica, 46, 226-232 (1991).
Koblenzer, C.S. "Neurotic excoriations and dermatitis artefacta," Dermatologic Clinics, vol. 14(3): 447-455 (Jul. 1996).
Tauberg, J. et al., "Stress-induced urticaria associated with local anesthetic administration," Anesthesia Progress, vol. 30(6): 199-200 (1983).
Theoharides, T.C. "Mast Cells: The Immune Gate To The Brain," Life Sciences, vol. 46: 607-617 (1990).
Lambracht-Hall, M. et al., "Serotonin Release From Rat Brain Mast Cells in Vitro," Neuroscience, vol. 39(1) 199-207 (1990).
Dimitriadou, V. et al., Histochemical and Ultrastructural Characteristics of Rat Brain Perivascular Mast Cells Stimulated With Compound 48/80 and Carbachol, Neuroscience, vol. 39(1): 209-224 (1990).
Pearce, F.L. "Mast cell heterogeneity," TIPS: 165-167 (Apr. 1983).
Theoharides, T.C. and Douglas, W.W. "Somatostatin Induces Histamine Secretion From Rat Peritoneal Mast Cells," Endocrinology, vol. 102(5): 1637-1640) (Nov. 7, 1977).
Sundaram, K. et al., "Antagonists of luteinizing hormone releasing hormone bind to rat mast cells and induce histamine release," Agents and Actions, vol. 25(3/4): 307-313 (1988).
Mathias, J. et al., "Debilitating 'Functional' Bowel Disease Controlled by Leuprolide Acetate, Gonadotropin-Releasing Hormone (GnRH) Analog," Digestive Diseases and Sciences, vol. 34(5): 761-766 (May 1989).
Read, N.W. "Irritable bowel syndrome (IBS)—definition and pathophysiology,", vol. 130: 7-13 (1987).
Stefanini, G.F. et al., "Oral disodium cromoglycate treatment on irritable bowel syndrome: An open study on 101 subjects with diarrheic type," vol. 87: 55-57 (1992).
International Search Report issued for PCT/US95/01392, dated May 31, 1995 (4 pages).
Hendriks, J. et al., "Flavonoids Influence Monocytic CTPase Activity and Are Protective in Experimental Allergic Encephalitis," J. Exp. Med., vol. 200(12): 1667-1672 (2004).
Mezzapesa, D. et al., "Glatiramer acetate in multiple sclerosis," Expert Rev. Neurotherapeutics (5)4: 451-458 (2005).
Gupta, E. et al., "Lovastatin and Extended-Release Niacin Combination Product: The First Drug Combination for the Management of Hyperlipidia," Heart Disease, vol. 4, 124-137 (2002).
Owens, M.J. and Nemeroff, C.B., "Physiology and Pharmacology of Corticotropin-releasing Factor," Pharmacological Reviews, vol. 43(4): 425-615 (1991).
Devlin, Thomas (ed): Textbook of Biochemistry with Clinical Correlations, 2nd Edition: Ch. 8.5-8.6, 345-351 (1982).
Simopoulos, A.P., Visioli F. (eds): Mediterranean Diets. World Rev. Nutr. Diet. Basel, Karger, vol. 87: 56-77 (2000).
Urade, Y. et al., "The Major Source of Endogenous Prostaglandin D2 Production is Likely Antigen-Presenting Cells," J. Immunol., 143(9): 2982-2989 (Nov. 1, 1989).
Lidor, C. et al., "Osteoporosis as the Sole Presentation of Bone Marrow Mastocytosis," J. Bone Min Res., vol. 5(8): 871-876 (1990).
Kimata, M. et al., "Effects of luteolin, quercetin and baicalein on immunoglobulin E-mediated mediator release from human cultured mast cells," Clin. and Exper. Allergy, vol. 30, 501-508 (2000).
Letters to the Editor, J. Allergy Clin. Immunol., vol. 119(2): 498-499 (Oct. 18, 2006).
Irani, A-M, et al., "Mast Cell Changes in Scleroderma," Arth. and Rheuma., vol. 35(8): 933-939 (Aug. 1992).
Dunn, R.T. et al., "Low-Dose Aspirin and Ibuprofen Reduce The Cutaneous Reactions Following Niacin Administration," Am. J. Thera., 2: 478-480 (1995).
Dvorak, A.M. et al., "Human Gut Mucosal Mast Cell: Ultrastructural Observations and Anatomic Variation In Mast Cell-Nerve Associations in vivo," Int. Archives of Allergy & Immunology, vol. 98: 158-168 (1992).
Cefali, E.A. et al., "Aspirin reduces cutaneous flushing after administration of an optimized extended-release niacin formulations," Int. J. Clin. Pharm. Ther., vol. 45: 78-88 (2007).
Verbeek, R. et al., "Oral flavonoids delay recovery from experimental autoimmune encephalomyelitis in SJL mice," Biochem. Pharm., 70: 220-228 (2005).
Trichopoulou, A. et al., "Diet and Survival of Elderly Greeks: a link to the past1-4. " Am. J. Clin. Nutri., vol. 61(suppl.): 1346S-50S (1995).
Tsakalos, N, et al., "Induction of Mast Cell Secretion by Parathormone," Biochemical Pharmacology, vol. 32(2): 355-360 (1983).

Theoharides, T. et al., "Bladder Mast Cell Activation in Interstitial Cystitis," Seminars of Urology, vol. IX(2): 74-87 (May 1991).

Shoskes, D., et al., "Quercetin in men with category III chronic prostatis: a preliminary prospective, double-blind, placebo-controlled trial," Urology, 54(6): 960-963 (1999).

Seibold, J. et al., "Dermal Mast Cell Degranulation in Systemic Sclerosis," Arth. and Rheuma., vol. 33(11): 1702-1709 (Nov. 1990).

Rockoff, S.D. and Armstrong, J.D. "Parathyroid Hormone as a Stimulus to Mast Cell Accumulation in Bone," Calc. Tiss. Res., 5: 49-55 (1970.

Morrow, J.D., et al., "Release of markedly increased quantities of prostaglandin D2 in vivo in humans following the administration of nicotinic acid," Prostaglandins, vol. 38(2): 263-274 (1989).

Boushey, R. et al., "Adrenal Cortical Carcinoma," Curr. Treatment Op. Oncol., 2: 355-364 (2001).

Chines, A. et al., "Systemic Mastocytosis Presenting as Osteoporosis: A Clinical and Histomorphometric Study," J. Clin. Endocrinol. and Metab., vol. 72(1): 140-144 (1991).

* cited by examiner

| | 5 | 7 | 2' | 3' | 4' | 5' |
|---|---|---|---|---|---|---|
| Quercetin | OH | OH | – | OH | OH | – |
| Kaempferol | OH | OH | – | – | OH | – |
| Myricetin | OH | OH | – | OH | OH | OH |
| Morin | OH | OH | OH | – | OH | – |

Figure 1

(a) A time course of ear temperature increase ($n=5$) in response to a single i.p. niacin (7.5 mg per rat) injection. The increase at all time points was significant (* $P=0.0002$). (b) Dose-response of the effect of a single i.p. niacin injection on ear temperature increases recorded 45 min later ($n=5$; * $P=0.0001$). Niacin rat doses correspond to the doses in an 80 kg human as follows: 5.0 mg per rat=1167 mg per human; 7.5 mg per rat=1750 mg per human; 10 mg per rat=2334 mg per human.

Figure 2

Comparison of the inhibitory effect of fisetin, kaempferol, luteolin, myricetin, quercetin (4.3 mg per rat=1000 mg per human) and aspirin (ASA; 1.22 mg per rat; 325 mg per human), administered i.p. 10 min prior to niacin on the ear temperature increase recorded 45 min after a single i.p. dose of niacin (7.5 mg per rat) in olive oil ($n=6$, * $P=0.0204$;  $P=0.0041$; * $P=0.0002$; **** $P=0.0193$). The percentage inhibition was calculated after the corresponding baseline temperature was subtracted.

Figure 3

Time course of the inhibitory effect of pretreatment with luteolin (4.3 mg per rat). Luteolin was given at the time points shown before, or at the same time as (shown as 0 h), the single i.p. niacin injection (7.5 mg per rat). Increases in ear temperature ($n=3$) were measured 45 min after niacin treatment. All pretreatments produced statistically significant inhibition, compared to a control rat injected with 0.5 ml olive oil and 7.5 mg niacin ($^*P<0.001$).

Figure 4

Effect of aspirin (ASA; 1.22 mg per rat) and luteolin (4.3 mg per rat) administered 2 h prior to a single i.p. injection of niacin (7.5 mg per rat) on plasma $PGD_2$ levels measured 45 min later ($n=3$). Brackets indicate groups compared (* $P=0.014$; ** $P=0.0419$). $PGD_2$, prostaglandin $D_2$.

Figure 5

Effect of aspirin (ASA; 1.22 mg per rat) and luteolin (4.3 mg per rat) administered 2 h prior to a single i.p. injection of niacin (7.5 mg per rat) on plasma 5-HT levels measured 45 min later ($n=3$). Brackets indicate groups compared ($^*P=0.0263$).

Figure 6

METHOD FOR PROTECTING HUMANS AGAINST SUPERFICIAL VASODILATOR FLUSH SYNDROME

This application is a continuation-in-part of co-pending U.S. patent application Ser. No. 11/999,991, filed Dec. 10, 2007, which is a continuation-in-part of U.S. patent application Ser. No. 11/651,161, filed Jan. 10, 2007 now U.S. Pat. No. 7,759,307, which is a continuation-in-part of U.S. patent application Ser. No. 10/811,828, filed Mar. 30, 2004 (now abandoned).

SUBJECT OF THE INVENTION

The invention is generally related to the treatment of the flush syndrome. More specifically, the invention is related to the use of particular dietary supplements, medical foods, prescription products or other adjuvants to conventional approved medications for protection against superficial vasodilator flush syndrome ("SVFS") in humans.

SVFS is present in a related group of human conditions that includes carcinoid-induced flush, niacin-induced flush, mesenteric traction-induced flush, serotonin-induced flush, postmenopause-induced flush, alcohol-induced flush and monosodium glutamate ("MSG")-induced flush.

Niacin is the most potent agent for reversing the trend to increased serum levels of cholesterol and triglycerides and increasing levels of serum LDL, while also increasing levels of serum HDL. Unfortunately, compliance with the niacin treatment regimen is often compromised by the development of a feeling of cutaneous warmth and itching, especially in the face (flush), even with the use of slow or extended release niacin preparations. In about 75% of patients taking niacin, acetylsalicylic acid ("ASA") reduces the flush effects, but only about 30%.

Certain plant flavonoids that belong to the class of polypherols, found in citrus fruit pulp, seeds, sea weed) are now recognized as having anti-allergic, anti-inflammatory, anti-oxidant and cytoprotective properties. Only some flavonoids, e.g. flavonols such as quercetin and the flavones such as luteolin, inhibit mast cell activation.

Quercetin inhibits secretion from human activated mast and macrophages. However, other flavonoids may have opposite effects. Use of the term "bioflavonoids", "citrus flavonoids" or "soy flavonoids" in certain commercial products, therefore, provides little information, and may, indeed, include molecules that have detrimental effects; for example, soy contains isoflavones that have estrogen-like activity that worsens inflammatory conditions. As will be detailed below, quercetin and luteolin are the most potent anti-SVFS biochemicals in patients receiving niacin.

An important need, therefore, exists for compositions for administration to human patients being treated for cardiovascular conditions with niacin and/or other other compounds, who present with SVFS. This need has been fulfilled by the present inventor by the finding that certain biochemicals, known to inhibit mast cell-induced inflammatory diseases, can be used clinically to inhibit SVFS. Such methods have been discovered, and are described below.

SUMMARY OF THE INVENTION

The invention comprises a method for treating humans to avoid or lessen SVFS. The method involves the timely administration of compositions that contain a flavonoid compound having the basic structure of 2-phenyl-4H-1-benzopyran or its 4-keto counterpart, and, optionally, a sulfated proteoglycan, olive kernel extract ("OKE"), sulfated glucosamine, a serotonin antagonist, bitter willow extract, S-adenosylmethionine ("SAM"), vitamin B12, histamine-1 receptor antagonists, histamine-3 receptor agonists, folic acid, and long-chain polyunsaturated fatty acids, together with appropriate excipients and carriers, said compositions having improved absorption from the gastrointestinal tract, skin surface, and nasal and pulmonary surfaces, and anti-SVFS effects, wherein the SVFS effects are caused by treatment with niacin or by other similarly acting conditions said compositions to be administered as separate formulations administered along with, prior to or subsequent to administration of niacin or other SVFS-causing chemicals.

In preferred embodiments, the flavonoid compound used in the method of treatment is quercetin, luteolin, genistein, myricetin, kaempferol and/or their respective glycosides, the sulfated glucosamine is D-glucosamine sulfate, and the proteoglycan is non-bovine chondroitin sulfate.

In still other embodiments, serotonin inhibitors are used in anti-SVFS treatment formulations, which include prochlorperazine, cyproheptadine and azatadine.

In yet another embodiment, the inventive method of treatment uses compositions that protect humans against a variety of SVFSs, the compositions including a flavonoid compound, and, optionally, one or more of a non-bovine chondroitin sulfate, D-glucosamine sulfate, bitter willow extract, folic acid, vitamin B12 and a serotonin inhibitor.

In another embodiment, the composition used in the inventive method of treatment also contains OKE that improves the absorption of drugs across membrane barriers in the body, such as those of the intestine, skin and pulmonary alveoli, and also contributes its own content of useful polyphenols, slows the release of niacin, and has independent protective action on the cardiovasacular system.

DETAILED DESCRIPTION OF THE INVENTION

It has been discovered that SVFS due to a variety of etiologies, e.g., niacin administration, can be successfully treated or prevented in humans by the judicious administration of a composition containing a flavonoid compound or its glycoside counterpart, and, optionally, one or more of the group consisting of a sulfated proteoglycan, OKE, a sulfated D-hexosamine, a serotonin antagonist, bitter willow extract, a histamine-1 receptor antagonist, a histamine-3 receptor agonist, long chain polyunsaturated fatty acids, S-adenosylmethionine, folic acid and vitamin B12, wherein said compositions may, at least in the case of niacin-induced SVFS, be administered before, with, or subsequent to a dose of niacin.

The anti-SVFS compositions of the invention may be used together with serum cholesterol- and LDL-lowering statins, such as simvastatin, lavastatin, atorvastatin, rosuvastatin, fluvastatin, and provastatin in the treatment of patients also being treated with niacin OKE improves the transmembrane transport of difficultly-absorbable molecules, such as therapeutic doses of lipophilic flavonoids and niacin, in the intestine, bladder, mouth, skin and pulmonary alveoli, and the release of water soluble molecules.

The highly preferred flavonoids are luteolin and quercetin, which inhibit secretion of inflammatory molecules from mast cells, macrophages and blood platelets by affecting moesin, a unique 78 kDa mast cell protein [Theoharides e al. *J Pharm Exp Therap* 294:810 (2000)]. In addition to luteolin and quercetin, other flavonoids suitable in carrying out the invention include the quercetin glycoside rutin, myricetin, genistein, kaempferol, the kaempferol glycoside astragaline or the isoflavone phenoxodiol.

In the method of treating SVFS in human It is preferred that the sulfated proteoglycan is non-bovine chondroitin sulfate, which blocks mast cell activation, degranulation and consequent secretion of inflammatory biochemicals from the mast cells. Other natural sulfated proteoglycans suitable for practicing this invention include keratan sulfate, dermatan sulfate and hyaluronic acid sodium salt, as well as polysaccharides, glycoproteins or proteoglycans containing plant extracts such as aloe vera. The preferred biological source of the chondroitin sulfate is shark cartilage which is more-highly sulfated than the common commercial chondroitin sulfate isolated from cow trachea, and which also avoids the potential dangers associated with bovine sources, such as "mad cow disease."

The OKE component of the compositions used in the inventive method is preferably an unrefined (first pressing, filtered, oleic acid-related acidity <3%, water content <1%) extract product produced, for one source, on the island of Crete in Greece. This kernel extract product is especially prepared by applicant's process consisting essentially of: (1) harvesting first collection ripe olives, preferably in December; (2) compressing the oil from the flesh of the ripe olives; (3) washing the kernels remaining after step (2) with water to remove debris; (4) drying the washed kernels with a stream of hot air; (5) crushing the dried kernels to produce an extract; (6) extracting the extract from step (5) with an organic solvent (e.g., hexane, heptane, octane) plus steam; (7) removing particulate matter from the organic extract by centrifugation or microfiltering through 1-2 micron pore size filters; (8) evaporating the organic solvent and water from the clarified extract of step (7) by maintaining the extract at 86-100° C. while percolating helium (to avoid oxidation) through the fluid, which process reduces the water content to <1%, the acidity (as oleic acid) to <3%; and, the organic solvent to <1%; and (9) storing the final kernel extract product in the absence of air.

The applicant has found that the novel OKE surprisingly has the unique property of increasing absorption of the other components of the anti-SVFS treatment compositions through the oral, alveolar, bladder, intestinal mucosa or skin, and also adds its own content of important anti-oxidants, such as omega fatty acids (e.g., eicosapentanoic acid) and alpha tocopherol. The polyphenols found in such OKE also have anti-inflammatory effects in, for example, arthritis [Martinez-Dominguez et al., *Inflamm. Res.* 50:102 (2001)]. Sources of OKE were E.B.E.K., Inc., Commercial, Industrial Enterprises of Crete, 118 Ethnikis Antistasos, Heraklion, Crete, 71306, Greece, and Minerva Edible Oil Enterprises, 65 Tatoiou St., Oddideos, Attica, n addition to its usefulness in increasing the absorption of the compositions across, for example, the intestinal wall and the skin, OKE is useful in aiding the dissolution of other drugs prior to administration to a patient, and is useful in promoting the absorption of other difficultly-absorbable molecules, e.g., the HDL-increasing drug torcetrapib (DeNinno et al. U.S. Pat. No. 6,586,448), across intestinal mucosa, oral mucosa, nasal mucosa, bladder mucosa, and skin of patients.

Figure 1:
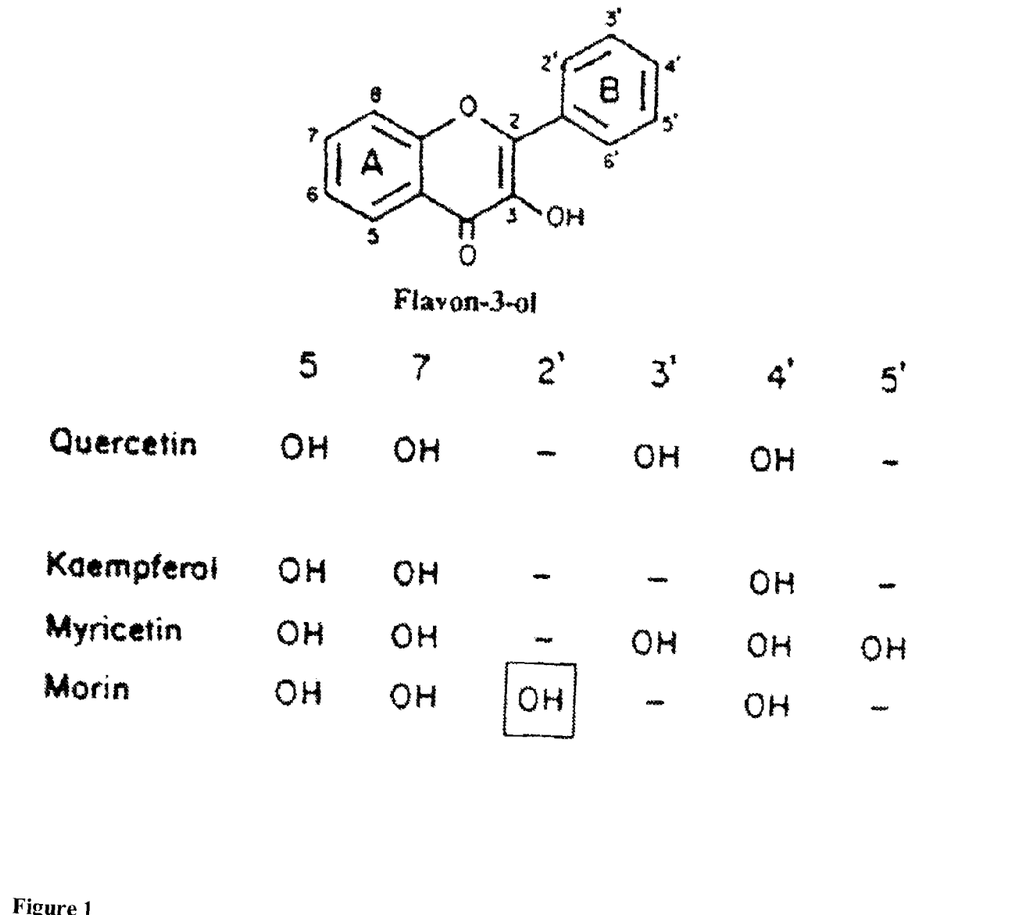
FIG. 1 shows the basic structure of a flavone compound, 2-phenyl-4H-1-benzopyran and its 4-keto counterpart, that are usedf in carrying out the inventive method. The active flavonoids differ mostly only in the presence or absence of hydroxyl groups at ring positions 5, 7, and 2'-5'.

Inhibitors of mast cell activation and consequent secretion of SVFS-inducing molecules such as PGD2 and serotonin in SVFS processes, such as in niacin-induced SVFS, and also in carcinoid, postmenopausal, mesenteric tfraction, serotonin, alcohol and MSG-induced SVFS (see Example 12, below). Applicant has discovered that certain flavonoid compounds of the basic structures 2-phenyl-4H-1-benzoyran and its 4-keto counterpart (described in the legend and figure of FIG. 1.), particularly, quercetin, luteolin, rutin, myricetin, genistein, inhibit niacin-induced flush syndromes in humans (Example 4) and in rat models (Example 5).

In experiments with rat models of the SVFS syndrome, applicant has surprisingly discovered that serotonin released from platelets, macrophages and mast cells, moderates the flush syndrome induced by niacin administration. This discovery has opened up a new therapeutic approach for niacin SVFS. Applicant has discovered that serotonin inhibitors/antagonists such as prochlorperazine, cyproheptadine, azatadine and ketanserin, when used alone or in combination with the basic compositions, inhibit the niacin-induced SVFS (Example 5, below).

Optional supplementation of the compositions described above with the methylation reagent S-adenosylmethionine ("SAM") adds antioxidant, anti-inflammatory and cytoprotective properties. Addition of SAM also accelerates metabolism of homocysteine, which amino acid has been implicated in coronary disease, to cysteine, which is harmless. Folic acid and vitamin B12 may be added to certain of the present formulations for similar reasons.

Another optional supplement to the basic compositions described above is a histamine-1 receptor antagonist, such as hydroxyzine, misolastine, azelastine, azatadine, ruputadine and cyproheptadine. Other histamine-1 receptor antagonists are described in Table 25-1 in Goodman and Gilman's The Pharmaceutical Basis of Therapeutics, 9th ed., New York, 1996.

The inventor has also found that flavonoid compounds alone or with the other components described below can neutralize the flush effects of as much as 300-3000 mg of niacin given concurrently. A highly preferred composition for preventing niacin-induced SVFS in human patients consists of 300-3000 niacin plus 300-3000 mg of luteolin, 10-150 mg folic acid, polyunsaturated fatty acids (300 mg in total), S-adenosyl methionine 50-400 mg, and white willow extract 200-2000 mg.

The preferred concentration range of the proteoglycan, hexosamine sulfate and flavonoid components of the oral formulations are 10-3,000 mg per tablet or capsule. The preferred concentration range for SAM is 30-1,000 mg per capsule or tablet. Generally, where present, the amounts of OKE are about equal to those of the total other active ingredients, preferably 300-1200 mg/capsule. The number of capsules or tablets to be taken per day is determined by the nature and severity of the medical condition, and is readily determinable by the patient's health provider. Other representative formulations are described in the examples below.

The compositions of the invention may be formulated in any standard means of introducing pharmaceuticals into a patient, e.g., by means of tablets or capsules. Standard excipients and carriers for the active ingredients of the inventive compositions are described in Remington's Pharmaceutical Sciences, Mack Publishing Co., Easton, Pa.

EXAMPLES

Example 1

Protecting Patients against Cardiovascular Disease with Niacin while Avoiding SVFS

|  | mg/capsule: |
|---|---|
| Niacin | 300-3000 |
| Luteolin | 100-3000 |
| Rutin | 100-5000 |
| S-adenosylmethionine | 50-400 |
| Folic acid | 10-150 |
| OKE | 350-1200 |
| Bitter willow bark extract | 5% by weight |
| Polyunsaturated fatty acids(DHA, DPA) | 100-600 |

Example 2

Protecting Against Niacin-Induced SVFS

| Ingredients, | mg per capsule: |
|---|---|
| Niacin | 300-3000 mg |
| Chondroitin sulfate | 50 mg |
| Quercetin or lutolein | 10-3500 mg |
| Optionally, OKE | 10-1200 |
| Bitter willow bark extract | 5% by weight |
| Optionally, cyproheptadine or azatadine | 1--8 |

Example 3

Effect of OKE Extract on Absorption of a Proteoglycan Sulfate In Vivo

Chondroitin sulfate was tritiated by New England Nuclear Corp. to a specific activity of 4.3 mCi/ml.

Unlabeled chondroitin sulfate was dissolved in OKE ratio of about 55 w/v chondroitin sulfate powder to about 450 w/v of OKE (2.9% acidity as oleic acid, 1.03% water, 0.08% hexane). To this solution was added 20.2 microcuries of the labeled chondroitin sulfate. AAA gelatin capsules were filled with the resulting solution using an aluminum template molding device.

The laboratory animals (250 g male Sprague-Dawley rats) were kept overnight without food but with free access to water. One capsule containing the above-described chondroitin sulfate-OKE solution was given to each rat per os. Control animals were given the equivalent amount of chondroitin sulfate, but without OKE. The animals were then given free access to food. Serum radioactivity was measured 8 hours thereafter in a beta scintillation counter.

The results showed that, in control animals, about 3.9%+/−0.4% (n=3) of the dose of labeled chondroitin sulfate reached the circulation. In sharp contrast, in animals given the labeled chondroitin sulfate mixed with OKE, about 14.3%+/−0.7% (n=4) of the dose was absorbed into the general circulation.

Similarly increased absorption was observed after mixing OKE with quercetin.

These results demonstrate that OKE increased by almost 400% the absorption of a proteoglycan from the intestine into the general circulation.

Parallel experiments with codfish oil, corn oil and olive oil (from the flesh of the olive) were contemplated, but chondroitin sulfate solubility in these oils was insufficient to meet the requirements of the experiment.

Example 4

Composition for Treating Niacin-Induced SVFS in Humans

Four normal male subjects (±28.4 years) were entered in the following protocol: On days 1 and 2, they were administered 1 gm immediate release niacin, at 2 pm. On days 3 and 4 they were administered 2 capsules of the anti-flush composition of Example 2 that contained 150 mg quercetin, 150 mg chondroitin sulfate, 150 glucosamine sulfate, and 450 mg of OKE per capsule. On days 4 and 6, they were administered the same antiflush capsules at 8 am and 1 g niacin, at 2 pm. Skin temperature was measured with an infrared digital pyrometer at 4 facial sites (forehead, both checks and chin) at 15, 30, 45, 60, 75 and 90 min post niacin administration, along with daily room temperature. Subjects also completed a symptoms questionnaire (erythema, edema, pruritus and burning sensation) on a scale of 0=no symptom and 5=maximal symptoms. There was no significant increase in temperature rise with niacin administration, but symptoms ranged 4-5 and lasted 3-4 hrs. After administration of the inventive composition, the scores were reduced to 2-3 and lasted only about 75 min. These results demonstrate that the inventive compositions containing a flavonoid will reduce niacin flush.

TABLE 1

| | Niacin alone/niacin + anti-flush composition | | | |
|---|---|---|---|---|
| | Day 2 | Day 2 | Day 3 | Day 4 |
| Erythema | 4.75 ± 0.5 | 4.5 ± 0.58 | 3.25 ± 0.5 | 2.5 ± 0.58 |
| Edema | 0.5 ± 0.58 | 0.5 ± 0.58 | 0.25 ± 0.5 | 0.25 ± 0.5 |
| Urticaria | 2.25 ± 0.5 | 2.0 ± 0.82 | 1.75 ± 0.5 | 1.25 ± 0.5 |
| Burning | 4.75 ± 0.5 | 4.0 ± 0.82 | 3.0 ± 0.82 | 2.5 ± 0.58 |
| Duration (hr) | 3.63 ± 1.11 | 2.75 ± 0.87 | 1.68 ± 0.40 | 1.68 ± 0.70 |

Example 5

Protection Against Niacin-Induced SVFS in an Animal Model

A. Niacin Alone

Niacin was administered to unanesthetized rats i.p., using 3 animals per dose.

| Dose, mg | Human equiv., mg |
|---|---|
| 2.5 | 583 |
| 5.0 | 1167 |
| 7.5 | 1750 |
| 10 | 2334 |

Figure 2:
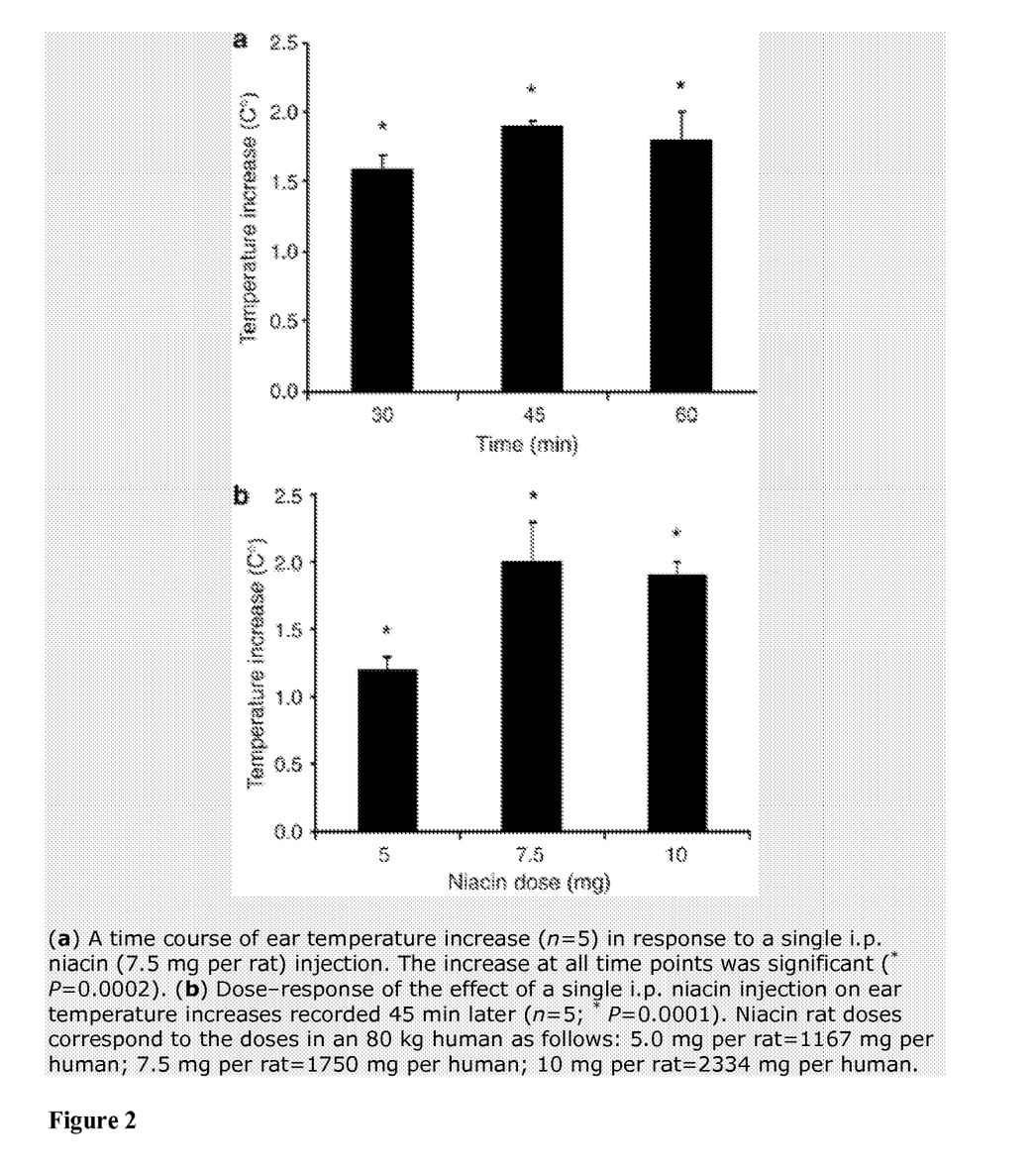
FIG. 2. (a) A time-course of ear temperature increase (n=5) in response to a single intraperitoneal (i.p.) injection of niacin (7.5 mg/rat) in a rat model for niacinm-induced flush. All time points were significant (p=0.0002). (b) Dose-response of the effect of a single i.p. niacin injection on ear temperature increases were recorded 45 min later (n=5). Niacin rat doses were based on 80 kg human (H) doses as follows: 5.0 mg/rat=1,167 mg/H; 7.5 mg/rat=1,750 mg/H; 10 mg/rat=2, 334 mg/H (p=0.0001).

Ear temperatures were determined 45 mins. after niacin administration. Baseline temperatures for rats is 26.5-28.5° C. Ear temperatures rose with all doses of niacin to a peak of +2 degrees C. (FIG. 2A)

B. Dose-Response Curves. (See. FIG. 2B)

Example 6

Comparison of Flavonoids for Anti-SVFS Effects

Figure 3:
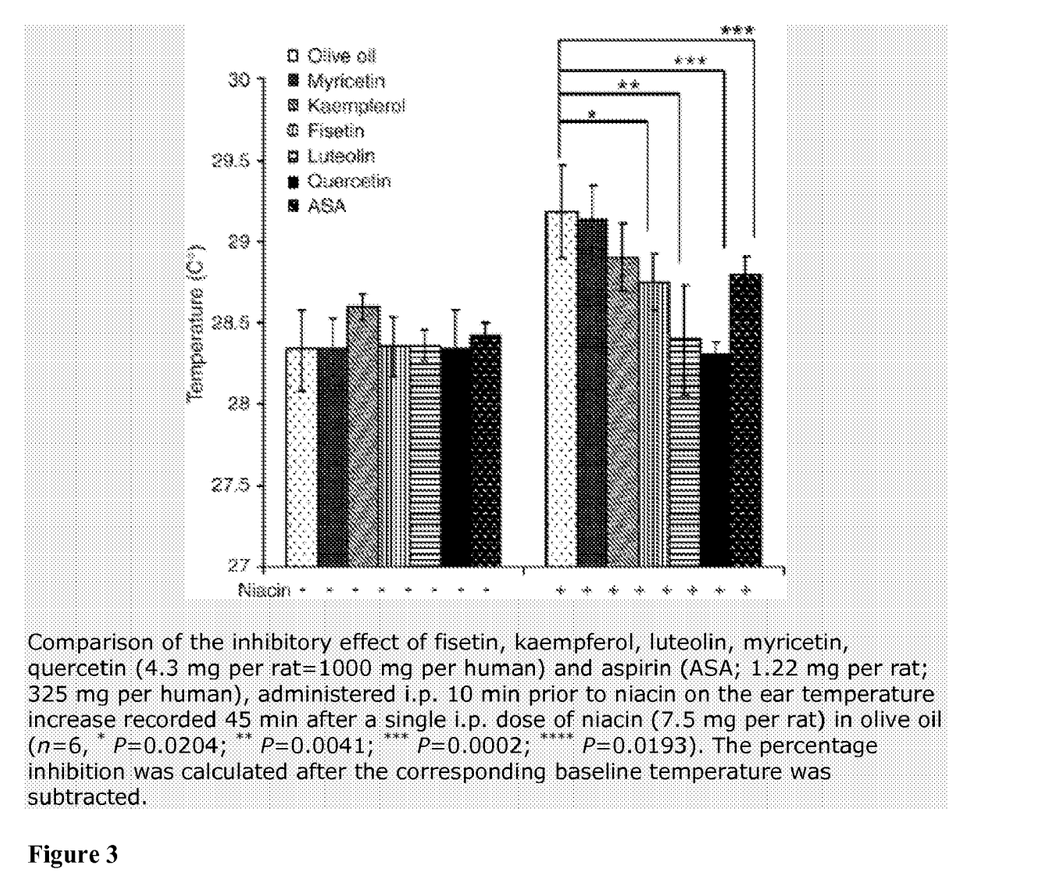
FIG. 3. Comparison of a family of anti-inflammatory flavonoids for anti-SVFS effectiveness.

Comparison of the inhibitory effect of fisetin, kaempferol, luteolin, myricetin, quercetin (4.3 mg per rat=1000 mg per human) and ASA, 1.22 mg per rat (325 mg per human), administered i.p. 10 min prior to niacin on the ear temperature increase recorded 45 min after a single i.p. dose of niacin (7.5 mg per rat) in olive oil (n=6, *P=0.0204; P=0.0041; *P=0.0002; ****P=0.0193). The percentage inhibition was calculated after the corresponding baseline temperature was subtracted. (FIG. 3)

Example 7

Comparison of Anti-SVFS Compounds

A. Treatment with Azatadine (Histamine-1 Receptor Antagonist).

Rats were treated with 17.1 ug of azatadine i.p. at time zero. Niacin, 5 mg, was given i.p. 30-480 mins. post-azatadine, and ear temperatures were measured.

At 10 mins. azatadine had reduced the niacin-induced temperature by 75%.

B. Treatment with Cyproheptadine (Strong Serotonin Receptor and Histamine-1 Receptor Antagonist)

Rats were treated with 8.55 ug of the antagonist i.p. at time zero, and niacin, 5 mg, was given at 120-480 mins.; thereafter. ear temperatures were measured at 45 mins.

Cyproheptadine blocked the effect of niacin in animals by 100% when the animals were pre-treated with ketotifen (H1 receptor antagonist).

Rats were pretreated with 17.1 ug of ketotifen, and niacin, 5 mg, was administered i.p. 30 mins; thereafter. ear temperatures were measured 45 mins. thereafter.

The drug had no significant effect on the niacin effect.

C. Treatment with Quercetin.

Quercetin, 4.7 mg, was given to rats i.p. at time zero, and 5 mg niacin administered i.p. 120, 240 and 360 mins. thereafter.

Figure 4:
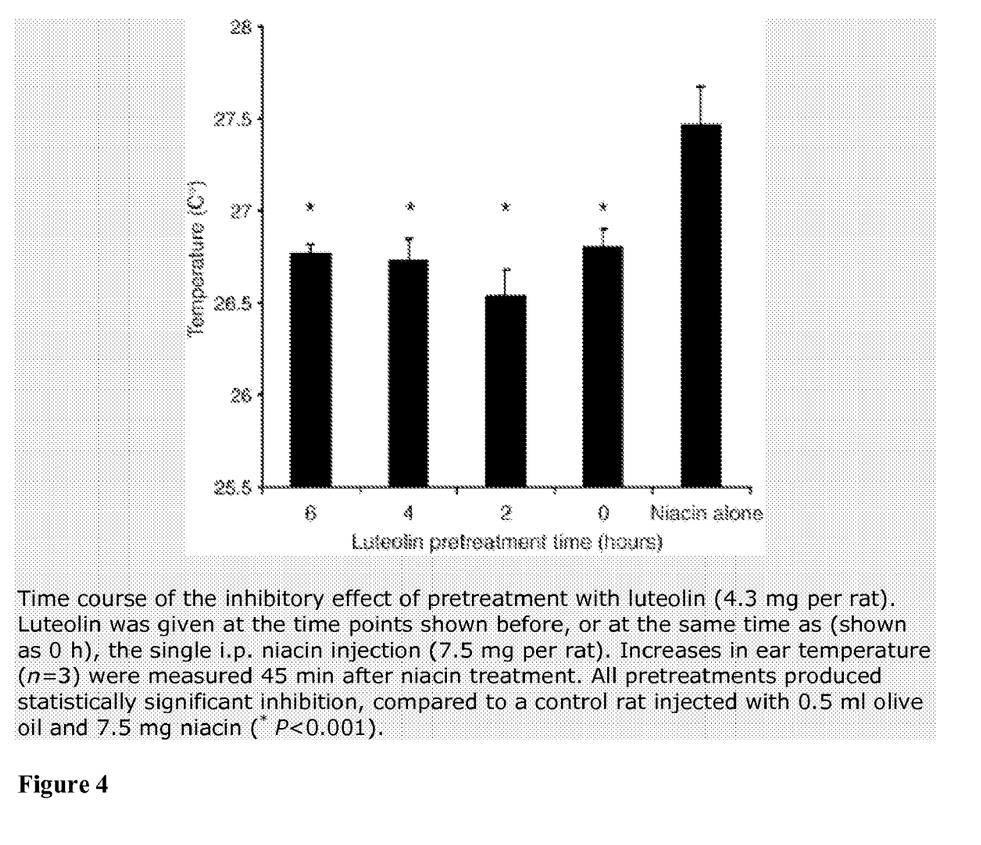
FIG. 4. Comparison of the inhibitory effect of fisetin, kaempferol, luteolin, myricetin, quercetin (4.3 mg/rat=1000 mg/80 kg human), and ASA (1.22 mg/rat), administered i.p. 10 min prior to niacin on the ear temperature increase recorded 45 min after a single i.p. injection of niacin (7.5 mg/rat) in olive oil (n=6, *p=0.0204, p=0.0041, *p=0.0002, ****p=0.0193). The percent inhibition was calculated after the corresponding baseline temperature was subtracted.

Quercetin inhibited the niacin effect by 100%. (FIG. 4)

Example 8

Time Course of the Effect of Luteolin on Rats

Figure 5:
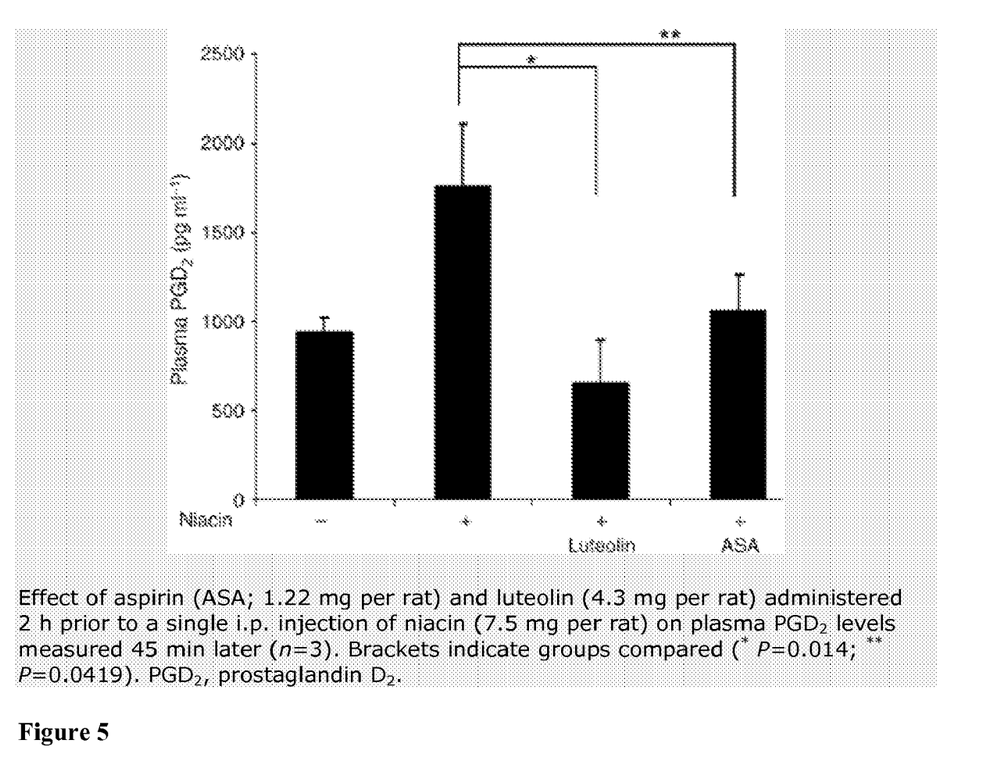
FIG. 5. Time course of the inhibitory effect of luteolin (4.3 mg/rat) pre-treatment (0=luteolin added together with niacin) on ear temperature increase (n=3) in response to a single i.p. injection of niacin (7.5 mg/rat), measured 45 min later. All time points were statistically significant as compared to a control rat injected with 0.5 ml olive oil and 7.5 mg niacin. Brackets indicate groups compared (*p<0.001).

When rats were pretreated with luteolin (4.3 mg/rat) at various time points prior to i.p. injection of 7.5 mg of niacin, and ear temperatures measured at 45", the flavonoid blocked the effect of niacin within 2 min. pre-niacin injection. FIG. 5).

Example 9

Effect of Aspirin or Flavonoids on Serum PGD2 Levels Induced by Niacin

Effect of ASP (1.22 mg/rat) and luteolin (4.3 mg per rat) administered i.p. 2 hrs previously to 7.5 mg/rat of niacin to a rat, and plasma PGD2 was measured at the 45" time point. Luteolin reduced the SVFS effect of niacin by about 50% at 45".

Figure 6:
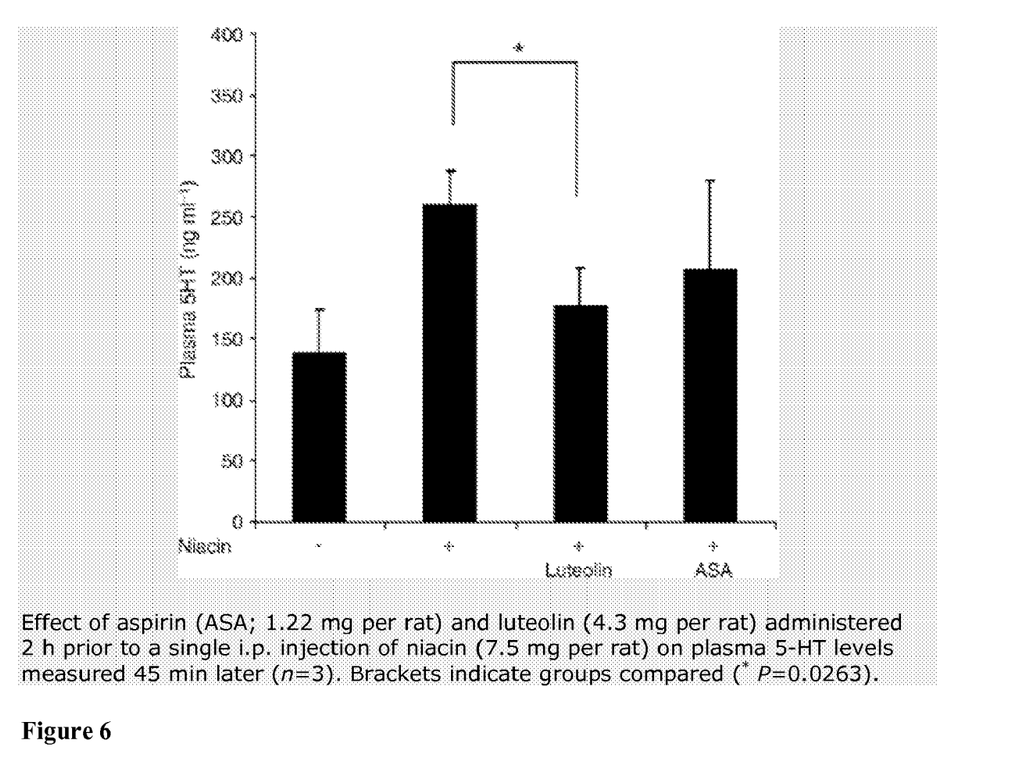
FIG. 6. Effect of ASA 1.22 mg/rat) and luteolin (4.3 mg/rat) administered 2 hr prior to a single i.p. injection of niacin (7.5 mg/rat) on plasma prostaglandin D2 ($PGD_{2)}$) levels measured 45 min later (n=3). Bracket indicate groups compared (*p=0.014; **p=0.0419).

ASP had a substantially lesser effect on SVSF than did luteolin (FIG. 6).

I claim:

1. A method for treating niacin-induced flush comprising administering to a patient in need thereof, a composition comprising an effective dose of a flavonoid compound, a non-bovine sulfated proteoglycan and olive kernel oil, wherein said flavonoid is selected from quercetin and luteolin.

2. The method of claim 1 wherein the method further comprises administration of cyproheptadine, prochlorperazine or azatadine.

3. The method of claim 1 additionally comprising administration of 300-3,000 mg of niacin.

4. The method of claim 3, wherein said niacin is in a form selected from the group consisting of an immediate release form, a slow release form, an extended release form and a sustained release form.

5. The method of claim 4, whereby said niacin is administered with an additional composition that lowers total serum cholesterol or lowers LDL cholesterol.

6. The method of claim 5, wherein said additional composition that lowers total serum cholesterol or lowers LDL cholesterol is a statin.

7. The method of claim 6, wherein said statin is selected from the group consisting of simvastatin, l-lovastatin, atorvastatin, rosuvastatin, fluvastatin and pravastatin.

8. The method of claim 3, wherein the niacin is an extended release niacin.

9. The method of claim 3, wherein said niacin is formulated with a prostaglandin D2 blocker.

10. The method of claim 9, wherein said blocker is selected from the group consisting of cyclooxygenase inhibitors and prostaglandin D2 receptor antagonists.

* * * * *